United States Patent [19]
Ortiz et al.

[11] Patent Number: 5,398,670
[45] Date of Patent: Mar. 21, 1995

[54] LUMEN TRAVERSING DEVICE

[75] Inventors: Mark S. Ortiz, Milford; Jack B. Stubbs, Waynesville, both of Ohio

[73] Assignee: Ethicon, Inc., Cincinnati, Ohio

[21] Appl. No.: 114,514

[22] Filed: Aug. 31, 1993

[51] Int. Cl.$^6$ .............................................. A61B 1/00
[52] U.S. Cl. .......................................... 128/6; 604/95; 385/119
[58] Field of Search ......................... 128/4, 6; 604/95; 385/116, 118, 119; 358/98

[56] References Cited

U.S. PATENT DOCUMENTS

| | | | |
|---|---|---|---|
| 3,557,780 | 1/1971 | Sato | 128/4 |
| 4,148,307 | 4/1979 | Utsugi | |
| 4,176,662 | 12/1979 | Frazer | |
| 4,224,929 | 9/1980 | Furihata | |
| 4,456,011 | 6/1984 | Wainecke | |
| 4,690,131 | 9/1987 | Lyddy, Jr. et al. | |
| 4,976,524 | 12/1990 | Chiba | 350/432 |
| 5,090,259 | 2/1992 | Shishido et al. | 73/866.5 |
| 5,144,848 | 9/1992 | Uenishi et al. | |
| 5,156,142 | 10/1992 | Anaplioxis et al. | |
| 5,201,731 | 4/1993 | Makky | |
| 5,243,967 | 9/1993 | Hibino | 128/6 |
| 5,337,732 | 8/1994 | Grundfest et al. | |

FOREIGN PATENT DOCUMENTS

| | | | |
|---|---|---|---|
| 1278965 | 11/1961 | France | 604/95 |
| 3631352 | 3/1988 | Germany | 128/4 |
| 1431127 | 5/1984 | U.S.S.R. | |

OTHER PUBLICATIONS

Whelan et al, "Videoarthroscopy: Review and State of the Art, " *Arthroscopy: The Journal of Arthroscopic & Related Surgery*, 8(3):311–319, 1992.

Gilbert et al, "Displacement Analysis of The interior walls of a pipe using panoramic holo-interferometry"- *Proc. of SPIE's 1991 International Symposium on Optical and Optoelectronic Applied Science and Engineering*, San Diego, Calif., Jul. 21–26, 1991, pp. 128–134.

Fau et al, "Panoramic Endoscopy", *Proc. of SPIE's 1992 Optical Fibers in Medicine VII*, Los Angeles, Calif., Jan. 1992.

*Primary Examiner*—Richard J. Apley
*Assistant Examiner*—John Mulcahy
*Attorney, Agent, or Firm*—Killworth, Gottman, Hagan & Schaeff

[57] ABSTRACT

An instrument is provided for migration through a lumen of a tubular part. The instrument comprises a distal section including a distal bladder adapted to be inflated and deflated; a proximal section including a proximal bladder adapted to be inflated and deflated; and, an intermediate section including an intermediate bladder adapted to be inflated and deflated. A device is associated with the distal section. A coupler is interposed between the distal and intermediate sections for movably coupling the distal section to the intermediate section. A drive mechanism is coupled between the distal and intermediate sections for effecting movement of the distal section about the coupler. A controller is provided for selectively inflating and deflating the distal, proximal and intermediate bladders to effect migration of the distal, intermediate and proximal sections through the lumen.

23 Claims, 10 Drawing Sheets

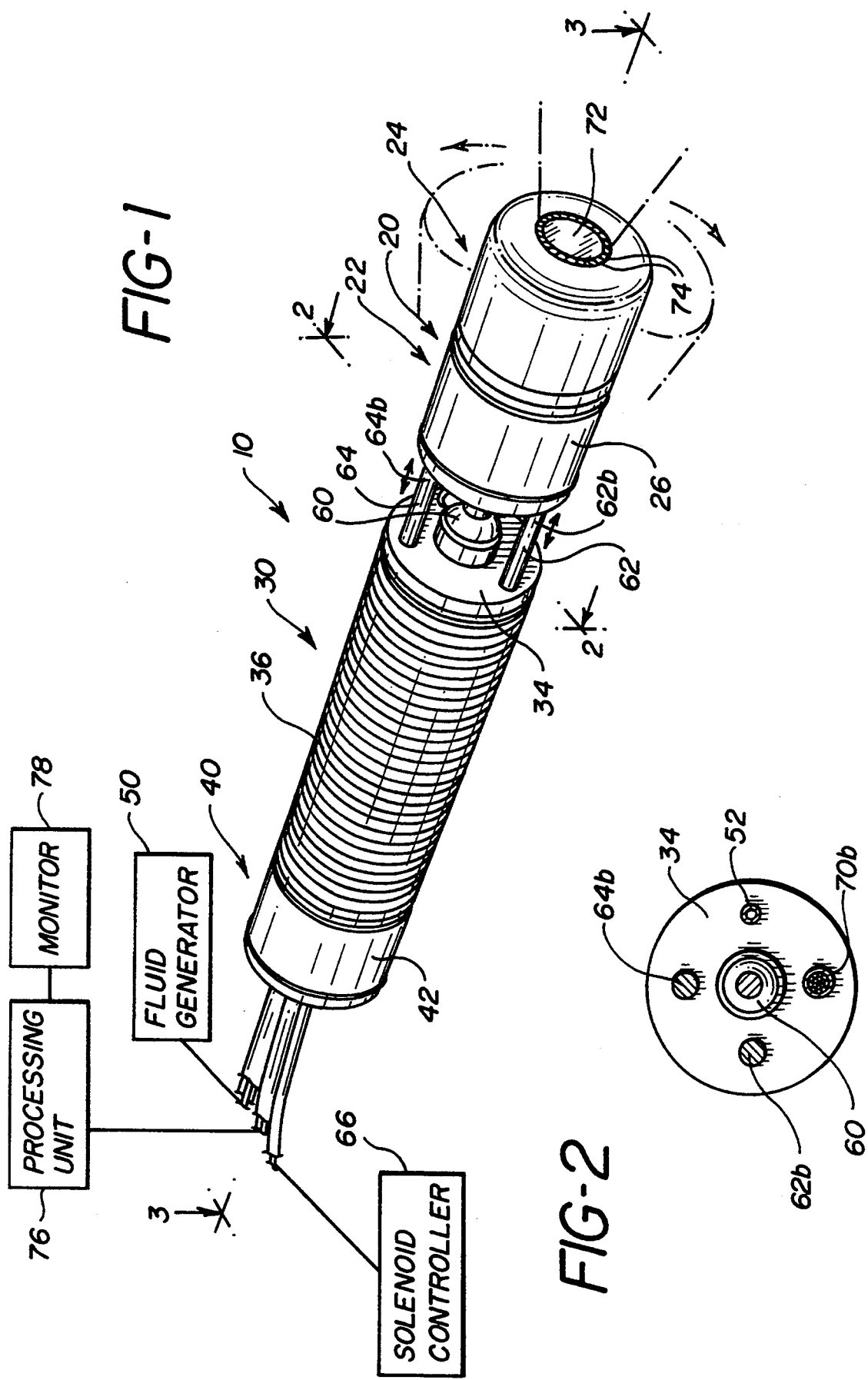

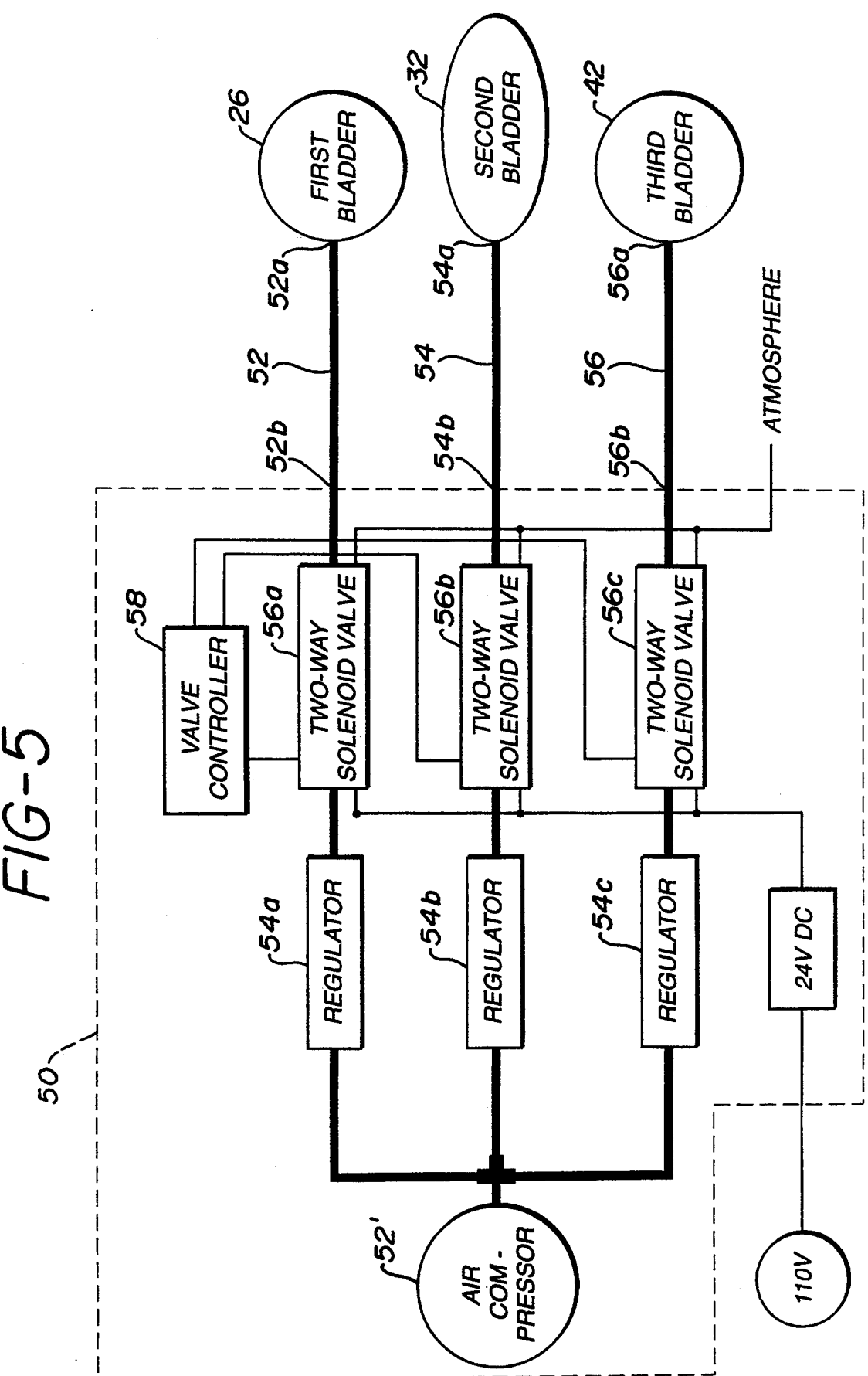

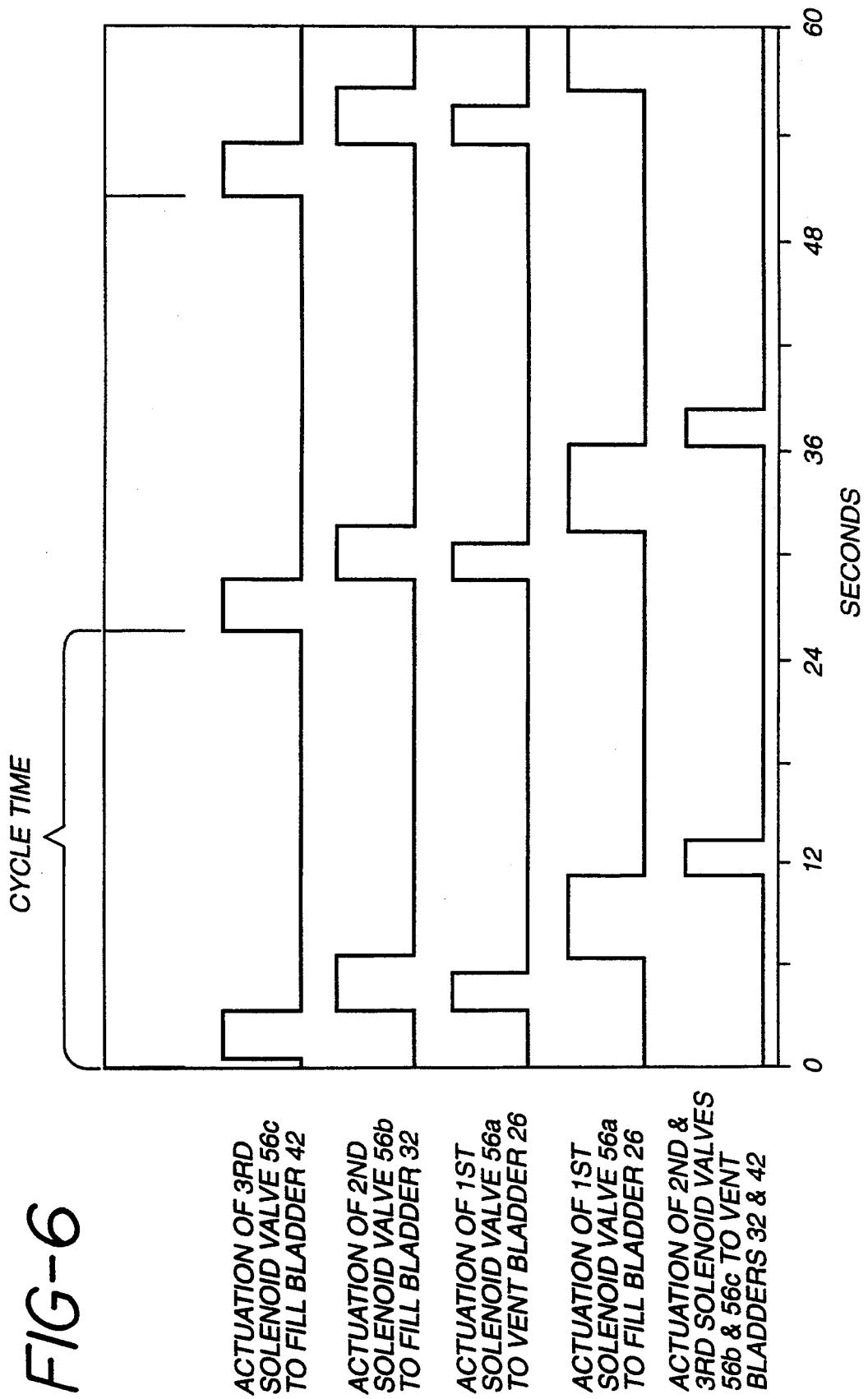

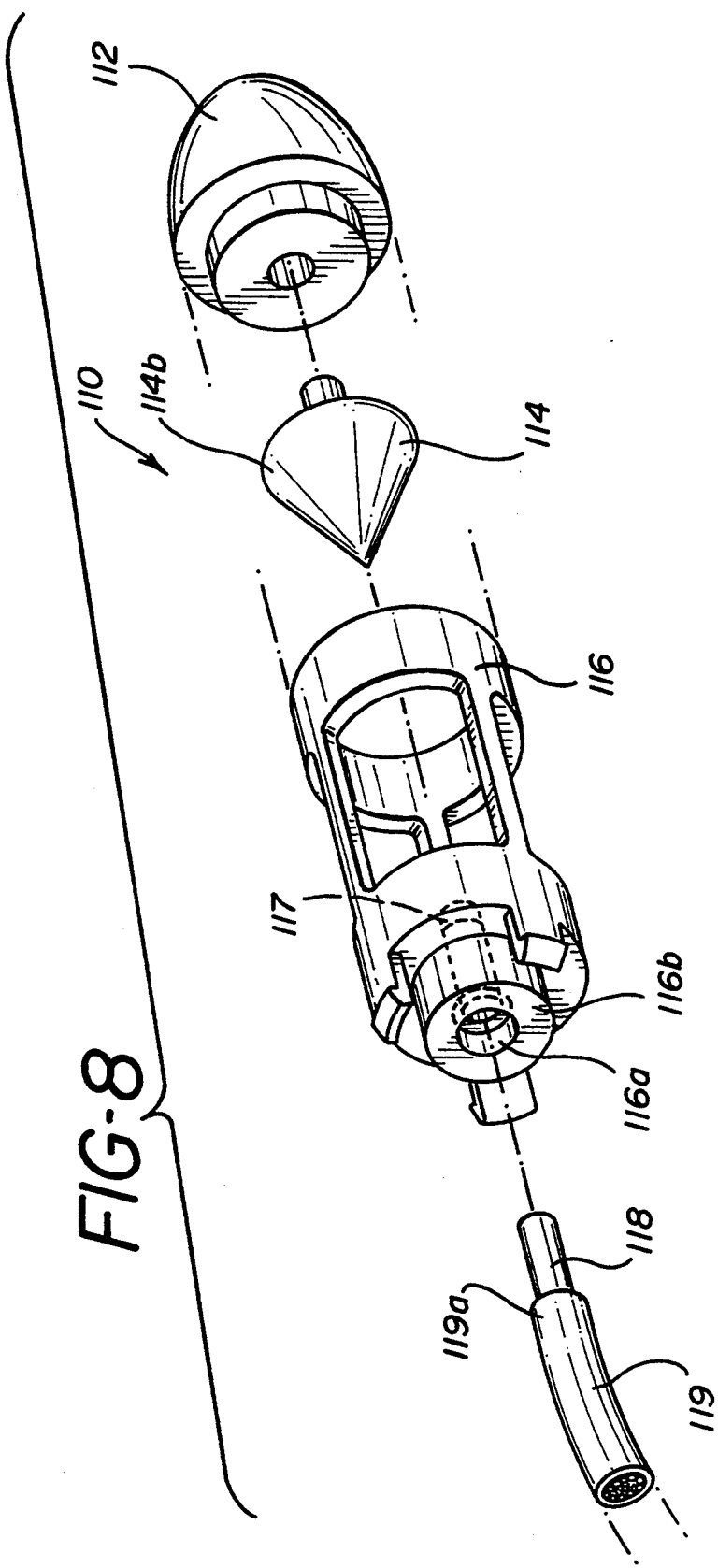

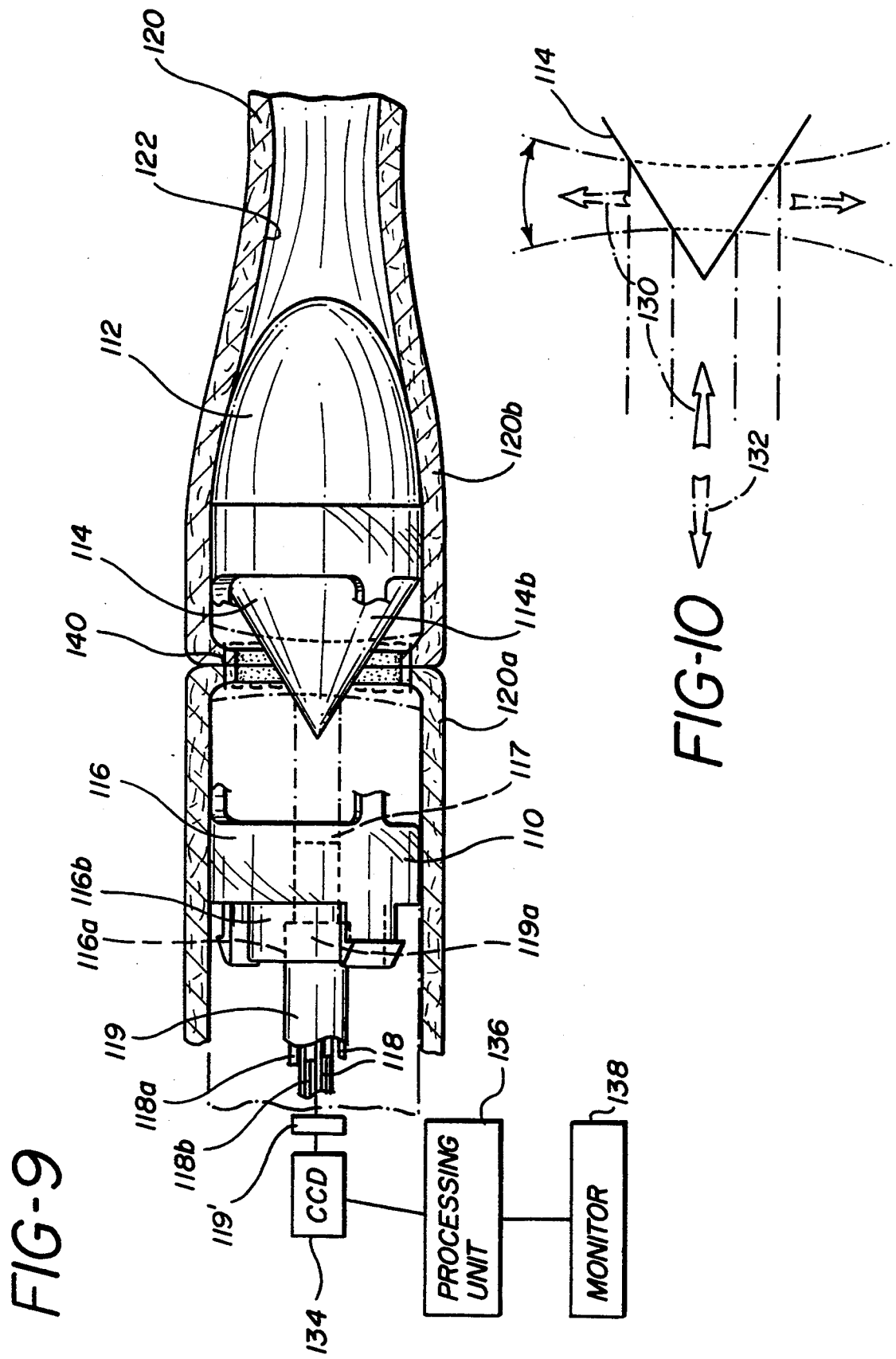

LUMEN TRAVERSING DEVICE

BACKGROUND OF THE INVENTION

The present invention relates generally to a medical instrument capable of migrating through a lumen of a tubular body part.

Medical instruments for migrating through a lumen of a tubular body part, such as the large intestine, are known in the prior art. For example, U.S. Pat. No. 4,176,662 discloses an endoscope provided with distal, intermediate and proximal inflatable cuffs. The cuffs are selectively inflated and deflated to effect migration of the distal end of the instrument through the lumen of a tubular body part. The instrument is provided with a sheath which encases a bundle of optical fibers. A first portion of the fibers transmits light from an external source through a window at the distal end of the instrument, while a second portion of the fibers transmits an image back to the proximal end of the instrument from the field of view of the window. The distal cuff is secured to the sheath and is radially expandable. The proximal and intermediate cuffs are secured to the distal and intermediate cuffs, respectively, and are axially slidable on the sheath. The proximal cuff is radially expandable while the intermediate cuff is axially expandable.

During a procedure involving use of an endoscope, such as the one disclosed in the noted patent, the instrument must be carefully navigated through the tubular body part in order to avoid perforating the intraluminal wall of the body part. While the instrument in the noted patent is disclosed as having a cuff propulsion mechanism at its distal end to pull the distal end through the tubular body part, it does not include coupler means interposed between a distal-most section of the instrument and an adjacent section for movably coupling the two sections to one another. Such coupler means would allow the distal-most section of the instrument to easily bend when it encounters a turn or a bend within the tubular body part. The instrument further lacks means for effecting angular movement of the distal-most section of the instrument about coupler means.

The referenced patent also fails to disclose a medical instrument adapted for intraluminal migration which includes means for permitting annular imaging of the intraluminal wall of a tubular body part. Annular inspections would be advantageous for screening intestines for polyps and cancer. The noted patent further fails to disclose a medical instrument adapted for intraluminal migration which includes a charge coupled device (CCD) for viewing the intraluminal wall of a tubular body part, or delivery means for delivering medication or a radiopaque agent to a desired portion of a tubular body part.

Accordingly, there is a need for a medical instrument adapted for intraluminal migration which includes a distal-most section coupled for movement with respect to the longitudinal axis of the instrument. There is further a need for a medical instrument adapted for intraluminal migration which includes at its distal-most section a medical device such as means for permitting annular imaging of the intraluminal wall of the tubular body part, a charge couple device for intraluminal inspection of the body part, or delivery means for delivering therapy to a desired portion of the tubular body part.

SUMMARY OF THE PRESENT INVENTION

These needs are met by the present invention wherein a medical instrument is provided for migrating through a lumen of a tubular body part. It includes a distal-most section capable of movement with respect to the longitudinal axis of the instrument. The distal-most section may be provided with means for permitting annular imaging of the intraluminal wall of the tubular body part, a charge couple device for intraluminal inspection of the body part, or delivery means for delivering air, water, light, electric or acoustic energy, medication or a radiopaque agent to a desired portion of the tubular body part.

In accordance with a first aspect of the present invention, a medical instrument is provided which is adapted for migration through a lumen of a tubular body part having an intraluminal wall. The instrument comprises a distal section including distal means for engaging and disengaging the intraluminal wall of the tubular body part; a proximal section including proximal means for engaging and disengaging the intraluminal wall of the tubular body part; and, an intermediate section including intermediate means for axially expanding and contracting. A medical device is associated with the distal section. Coupler means is interposed between the distal and intermediate sections for movably coupling the distal section to the intermediate section. Control means is further provided for selectively engaging and disengaging the distal and proximal means with the intraluminal wall and expanding and contracting the intermediate means to effect migration of the distal, intermediate and proximal sections through the lumen.

The medical device may comprise means for delivering a fluid, such as water or air, into the lumen of the tubular body part, means for delivering a therapy (e.g., light, medication, or electric, acoustic and other forms of energy) to a portion of the tubular body part, means for delivering a radiopaque agent to a portion of the tubular body part, imaging means for viewing the tubular body part (e.g., a charge couple device (CCD)), or optical means for permitting annular imaging of the intraluminal wall of the tubular body part for inspection thereof.

The medical instrument preferably further includes drive means coupled between the distal and intermediate sections for effecting movement of the distal section about the coupling means. The drive means may comprise one or more solenoids, or one or more shape-memory-alloy wires.

The distal means may comprise a distal bladder which is adapted to be radially expanded and contracted. The proximal means may comprise a proximal bladder which is adapted to be radially expanded and contracted. The intermediate means may comprise an intermediate bladder which is adapted to be axially expanded and contracted and means for biasing the distal and proximal sections toward one another.

In accordance with a second aspect of the present invention, a medical instrument is provided which is adapted for migration through a lumen of a tubular body part having an intraluminal wall. The instrument comprises a distal section including a first portion having distal means for engaging and disengaging the intraluminal wall of the tubular body part and a second portion; a proximal section including proximal means for engaging and disengaging the intraluminal wall of the tubular body part; and, an intermediate section including intermediate means for axially expanding and contracting. A medical device is associated with the second portion of the distal section. Drive means is provided for causing at least the second portion of the distal section and the medical device to move with respect to a longitudinal axis of the instrument. Control means is further provided for selectively engaging and disengaging the distal and proximal means with the intraluminal wall and expanding and contracting the intermediate means to effect migration of the distal, proximal and intermediate sections through the lumen.

In accordance with a third aspect of the present invention, a medical instrument is provided which is adapted for migration through a lumen of a tubular body part having an intraluminal wall. The device comprises a distal section including distal means for engaging and disengaging with the intraluminal wall of the tubular body part; a proximal section including proximal means for engaging and disengaging with the intraluminal wall of the tubular body part; and, an intermediate section including intermediate means for expanding and contracting. Optical means is associated with the distal section for permitting annular imaging of the intraluminal wall of the tubular body part to permit inspection thereof. The optical means may comprise a conical reflector. Control means is further provided for selectively engaging and disengaging the distal and proximal means with the intraluminal wall and expanding and contracting the intermediate means to effect migration of the distal, intermediate and proximal sections through the lumen.

In accordance with a fourth aspect of the present invention, an instrument is provided which is adapted for migration through a tubular part having an inner wall. The instrument comprises a distal section including a first portion having distal means for engaging and disengaging the inner wall of the tubular part and a second portion; a proximal section including proximal means for engaging and disengaging the inner wall of the tubular part; and, an intermediate section including intermediate means for axially expanding and contracting. A device for performing an operation within the tubular part is associated with the second portion of the distal section. Drive means is provided for causing at least the second portion of the distal section and the device to move with respect to a longitudinal axis of the instrument. Control means is further provided for selectively engaging and disengaging the distal and proximal means with the inner wall and expanding and contracting the intermediate means to effect migration of the distal, proximal and intermediate sections through the tubular part.

Accordingly, it is an object of the present invention to provide an instrument for migrating through a tubular part and which includes a distal-most section capable of movement with respect to the longitudinal axis of the instrument. It is further an object of the present invention to provide a medical instrument adapted for migration through a lumen of a tubular body part which includes means for permitting annular imaging of the intraluminal wall of the tubular body part. It is another object of the present invention to provide a medical instrument adapted for migration through a lumen of a tubular body part which includes a charge couple device for intraluminal inspection of the body part. It is yet a further object of the present invention to provide a medical instrument adapted for migration through a tubular body part which includes delivery means for delivering air, water, light, electric, acoustic and other forms of energy, medication or a radiopaque agent to a desired portion of the tubular body part. These and other advantages of the present invention will be apparent from the following description, the accompanying drawings and the appended claims.

BRIEF DESCRIPTION OF THE DRAWINGS

FIG. 1 is a perspective view of a medical instrument constructed in accordance with a first embodiment of the present invention;

FIG. 2 is a view taken along section line 2—2 in FIG. 1;

FIG. 5 is a schematic illustration of the fluid generator illustrated in FIG. 1;

FIG. 6 is a timing diagram for the first, second and third two-way solenoid valves of the fluid generator;

FIG. 8 is an exploded view of a second portion of the distal section of a medical instrument constructed in accordance with a second embodiment of the present invention;

FIG. 9 is a side view of the second portion in FIG. 8 with the window collar partially broken away;

FIG. 10, is a schematic illustration showing light reflected by the axicon shown in FIGS. 8 and 9;

DETAILED DESCRIPTION OF THE INVENTION

Figure 3:
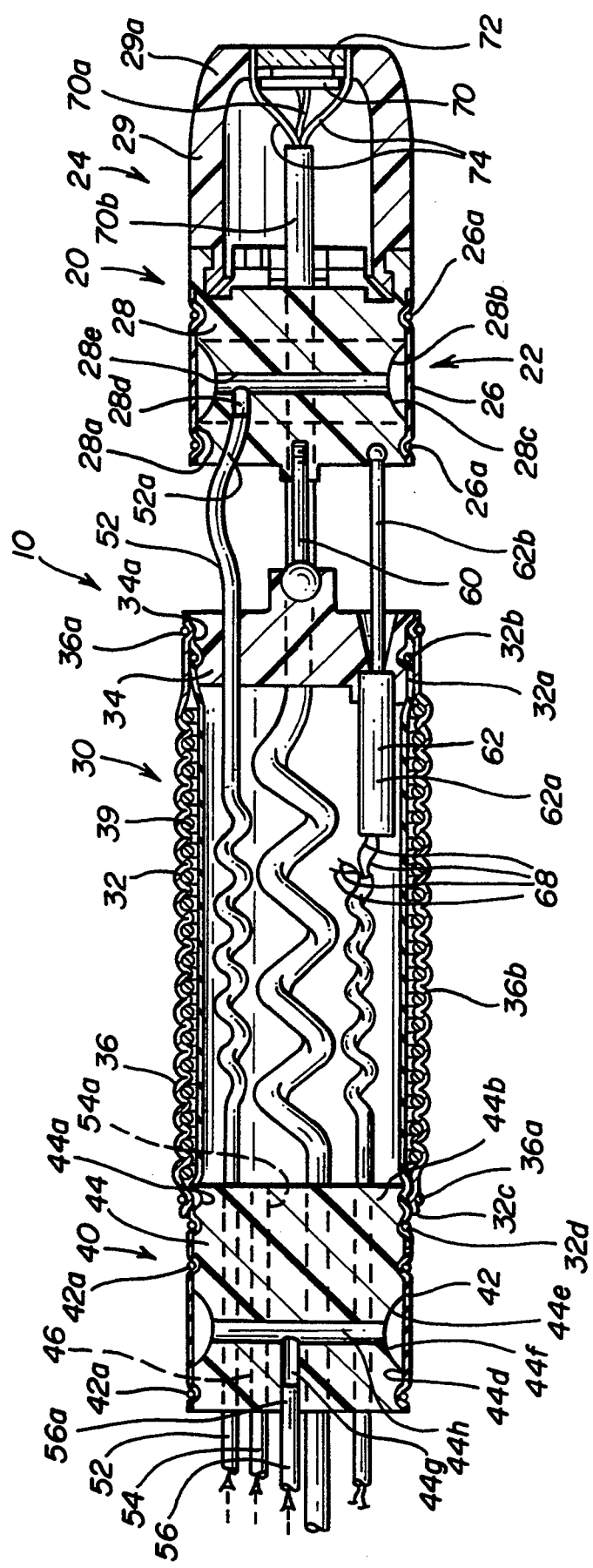
FIG. 3.is a view taken along section line 3—3 in FIG. 1.

A medical instrument adapted for migration through the lumen of a tubular body part is shown in FIG. 1, and is generally designated by the reference numeral 10. The instrument 10 includes a distal section 20, an intermediate section 30 and a proximal section 40. The distal section 20 comprises first and second portions 22 and 24, respectively. The first portion 22 includes a first bladder 26 which is radially expandable and contractible. The intermediate section 30 includes a second bladder 32 (see FIG. 3) which is axially expandable and contractible, and the proximal section 40 includes a third bladder 42 which is radially expandable and contractible. The first, second and third bladders 26, 32 and 42 are formed from latex, silicone or a like polymeric material. As will be discussed more explicitly below, the first, second and third bladders 26, 32 and 42 are selectively expanded and contracted by a fluid generator 50 to effect migration of the distal, intermediate and proximal sections 20, 30 and 40 through the lumen of a tubular body part. The tubular body part may comprise, for example, the large and small intestines of a human body.

As shown in FIG. 3, the first portion 22 further includes a first member 28 formed from a polymeric material, such as polycarbonate or polyetherimide, which polymers are commercially available under the tradenames Lexan and ULTEM, respectively, from the General Electric Company. The first member 28 may also be formed from a metal. The first member 28 generally cylindrical in shape and includes an outer circumferential surface 28a. A central portion 28b of the outer circumferential surface 28a extends inwardly to define an annular recess 28c. The first member 28 further includes first and second bores 28d and 28e, respectively. The first bore 28d receives the distal end 52a of a first fluid line 52. The second bore 28e communicates with the first bore 28d and the annular recess 28c.

Figure 4:
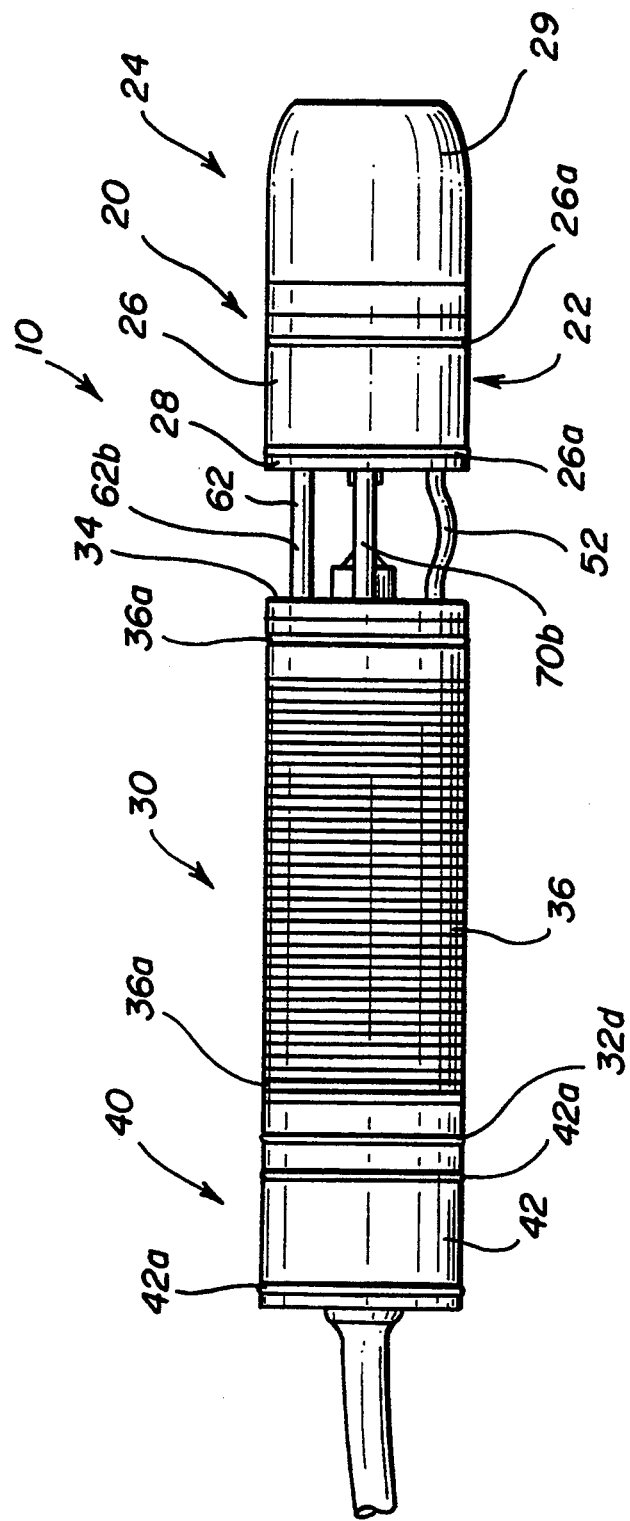
FIG. 4 is a side view of the medical device in FIG. 1.

The first bladder 26 is positioned about the outer circumferential surface 28a of the first member 28 and extends across the annular recess 28c. In the illustrated embodiment, the first bladder 26 is secured to the first member 28 by thread 26a, see also FIG. 4. Other known attachment means, such as adhesive material (not shown), may be used in addition to or in place of the thread 26a.

The proximal end 52b of the first fluid line 52 is connected to the fluid generator 50, see FIG. 5. The fluid generator 50 periodically generates first fluid pulses, air pulses in the illustrated embodiment, which are communicated to the annular recess 28c via the first fluid line 52 and the first and second bores 28d and 28e for radially expanding the first bladder 26. The generator 50 also periodically vents air from the bladder 26 to atmosphere to allow the bladder 26 to contract.

As shown in FIG. 3, the intermediate section 30 further includes a second member 34 which may be formed from the same material from which the first member 28 is formed. The distal end 32a of the second bladder 32 extends about the outer circumferential surface 34a of the second member 34 and is secured thereto by thread 32b. The proximal end 32c of the second bladder 32 extends about the outer circumferential surface 44a of a third member 44 and is secured thereto by thread 32d. The distal end 44b of the third member 44 defines the proximal end of the intermediate section 30. The third member 44 may be formed from the same material from which the first member 28 is formed.

An outer cloth bellows 36 encases the second bladder 32 and is secured to the second and third members 34 and 44 by thread 36a. In the illustrated embodiment, a spring 39 is secured to the inner surface 36b of the bellows 36 by adhesive material or similar attachment means. The spring 39 serves to bias the distal and proximal sections 20 and 40 toward one another. Alternatively, the spring 39 could be located within the second bladder 32 and secured to the second and third members 34 and 44 for biasing the distal and proximal sections 20 and 40 toward one another. It is further contemplated by the present invention that the second bladder 32 and the spring 39 could be replaced by a solenoid (not shown) or a piston-cylinder unit (not shown) coupled between the second and third members 34 and 44.

The distal end 54a of a second fluid line 54 extends through a bore 46 in the third member 44 and communicates with the second bladder 32. The proximal end 54b of the second fluid line 54 is connected to the fluid generator 50, see FIG. 5. The fluid generator 50 periodically generates second fluid pulses which are communicated to the second bladder 32 via the second fluid line 54 for axially expanding the second bladder 32. Expansion of the second bladder 32 causes the second member 34 and, hence, the distal section 20 to move away from the third member 34, which forms part of the proximal section 40. The generator 50 also periodically vents air from the bladder 32. Ventilation of air from the bladder 32 allows the distal and proximal sections 20 and 40 to move toward one another as a result of the spring 39 biasing the second and third members 34 and 44 together.

The third bladder 42 extends about the outer circumferential surface 44d of the third member 44 and is secured thereto by thread 42a. A central portion 44e of the outer circumferential surface 44d extends inwardly to define an annular recess 44f. The third bladder 42 extends across the annular recess 44f. The third member 44 further includes first and second passages 44g and 44h, respectively. The first passage 44g receives the distal end 56a of a third fluid line 56. The second passage 44h communicates with the first passage 44g and the annular recess 44f.

The proximal end 56b of the third fluid line 56 is connected to the fluid generator 50, see FIG. 5. The fluid generator 50 periodically generates third fluid pulses which are communicated to the annular recess 44f via the third fluid line 56 and the first and second passages 44g and 44h for radially expanding the third bladder 42. The fluid generator 50 also periodically vents air from the bladder 42 to allow the bladder 42 to contract.

A ball and socket coupler 60 is interposed between the distal section 20 and the intermediate section 30 to movably couple the distal section 20 to the intermediate section 30.

First and second solenoids 62 and 64 are coupled between the distal and intermediate sections 20 and 30 to effect movement of the distal section 20 about the coupler 60, see FIGS. 1 and 3. The first solenoid 62 includes a base portion 62a which is fixedly mounted within the second member 34. The first solenoid 62 further includes a first flexible, reciprocating articulation rod 62b which extends out from the base portion 62a. The distal end of the rod 62b is attached to the first member 28. The second solenoid 64 includes a base portion (not shown) which is fixedly mounted within the second member 34 and spaced approximately 90° from the base portion 62a. The second solenoid 64 further includes a second flexible, reciprocating articulation rod 64b which extends out from the base portion of the second solenoid 64. The second rod 64b is spaced approximately 90° from the first rod 62b, see FIG. 2, and its distal end is attached to the first member 28.

A solenoid controller 66 is connected to the solenoids 62 and 64 via conductors 68, see FIGS. 1 and 3. The controller 66 serves to actuate one or both of the solenoids 62 and 64 to effect angular movement of the distal section 20 about the coupler 60. The solenoid controller 66 may comprise two switches, a joystick, or other like control mechanism. Thus, a physician, via the controller 66, may articulate the distal section 20 of the instrument 10 as the section 20 encounters bends and turns during its movement through the length of a tubular body part. Because angular movement of the distal section 20 is possible, there is reduced risk that the distal section 20 might perforate the wall of the tubular body part as the three sections 20, 30 and 40 traverse the length of the tubular body part.

Referring again to FIGS. 1 and 3, the second portion 24 of the distal section 20 comprises an outer housing 29 which may be formed from the same material from which the first member 28 is formed. The housing 29 is snap-fitted onto the first member 28. Fixedly mounted at the distal end 29a of the housing 29 is an imaging device, a charge coupled device (CCD) 70 in the illustrated embodiment, a focusing lens 72 and distal ends of a plurality of light-emitting optical fibers 74. As best shown in FIG. 1, the fibers 74 are arranged circumferentially about the lens 72. The CCD 70 defines a plurality of pixels which sense light and generate voltage signals in response thereto. The CCD 70 is used in conjunction with a processing unit 76 which receives the voltage signals via conductors 70a, integrates those voltage signals and generates a video signal which is passed to a monitor 78. The monitor 78 displays a picture of the image sensed by the CCD 70. Thus, a physician, by viewing the monitor 78, can visually inspect the lumen of a tubular body part as the distal, intermediate and proximal sections 20, 30 and 40 traverse the length of the tubular body part. The fibers 74 and the conductors 70a are encased within a sheath 70b, see FIGS. 3 and 4.

Turning now to FIG. 5, the fluid generator 50 comprises an air compressor 52', first, second and third regulators 54a–54c, first, second and third two-way solenoid valves 56a–56c, and a valve controller 58, such as three switches, a programmable processor, or other like control mechanism. The regulators 54a–54c maintain the pressure of the air communicated to the solenoid valves 56a–56c from the compressor 52' at a substantially constant value. The first two-way solenoid valve 56a is associated with the first bladder 26. In response to a first fill signal from the controller 58, the first valve 56a opens for a time period sufficient to allow pressurized air to communicate with the recess 28c via the first fluid line 52 and the first and second bores 28d and 28e to inflate the first bladder 26. In response to a first vent signal from the controller 58, the first valve 56a opens for a time period sufficient to allow pressurized air in the first bladder 26 to vent to atmosphere.

The second valve 56b is associated with the second bladder 32. In response to a second fill signal from the controller 58, the valve 56b opens for a time period sufficient to allow pressurized air to communicate with the second bladder 32 via the second fluid line 54 to cause axial expansion of the second bladder 32. In response to a second vent signal generated by the controller 58, the second valve 56b opens for a time period sufficient to allow pressurized air in the second bladder 26 to vent to atmosphere. As the pressurized air is vented from the second bladder 32, the spring 39 causes the distal and proximal sections 20 and 40 to move toward one another.

The third valve 56c is associated with the third bladder 42. In response to a third fill signal from the controller 58, the valve 56c opens for a time period sufficient to allow pressurized air to communicate with the recess 44f via the third fluid line 56 and the first and second passages 44g and 44h to inflate the third bladder 42. In response to a third vent signal from the controller 58, the third valve 56c opens for a time period sufficient to allow pressurized air in the third bladder 42 to vent to atmosphere. Examples of actuation time periods for the valves 56a–56c are shown in FIG. 6. These time periods may be varied via the valve controller 58 in order to vary the rate of migration of the distal, intermediate and proximal sections 20, 30 and 40 through a tubular body part.

Figure 7A:
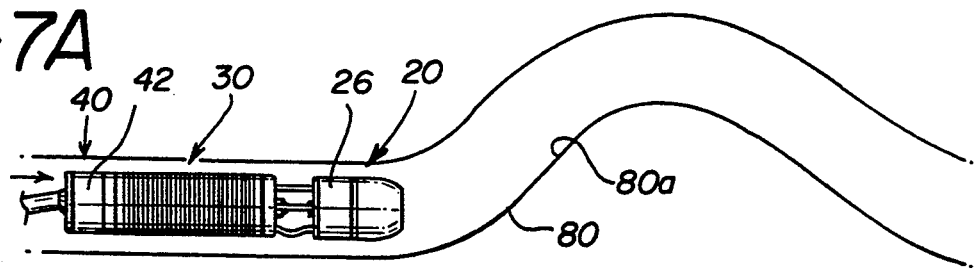
FIGS. 7A–7E are sequential illustrations showing the operation of the apparatus of FIG. 1.

Operation of the instrument 10 to effect the migration of the distal, intermediate and proximal sections 20, 30 and 40 through the lumen of a tubular body part 80 will now be described. Initially, the distal, intermediate and proximal sections 20, 30 and 40 are inserted into the lumen of the tubular body part 80, see FIG. 7A. The valve controller 58 is then activated to effect sequential actuation of the two-way solenoid valves 56a–56c in the manner illustrated in the timing chart of FIG. 6.

Figure 7B:
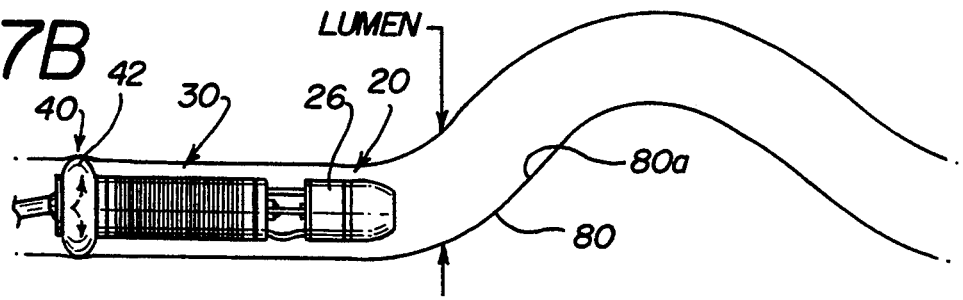
Figure 7C:
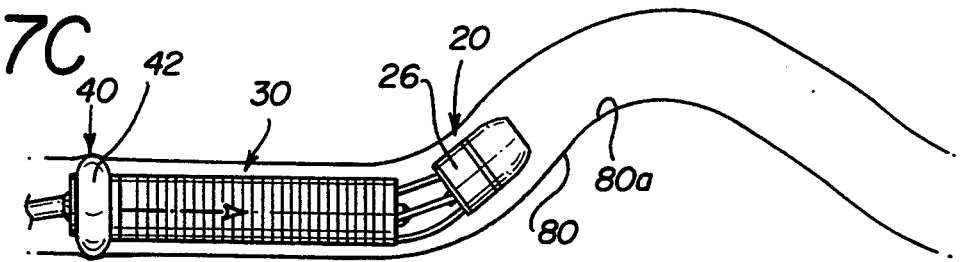
Figure 7D:
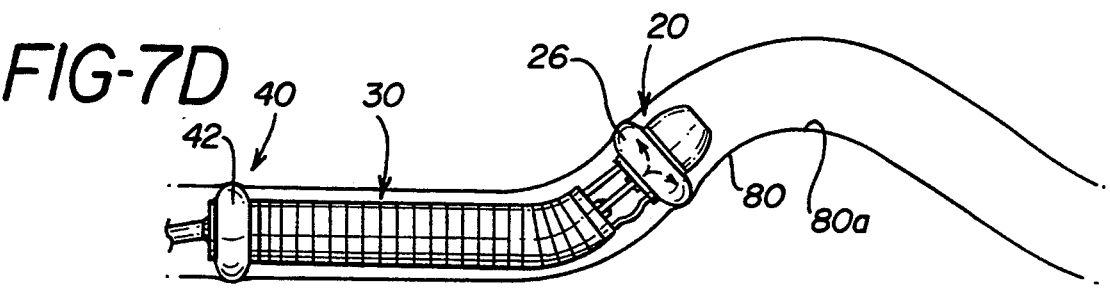
Figure 7E:
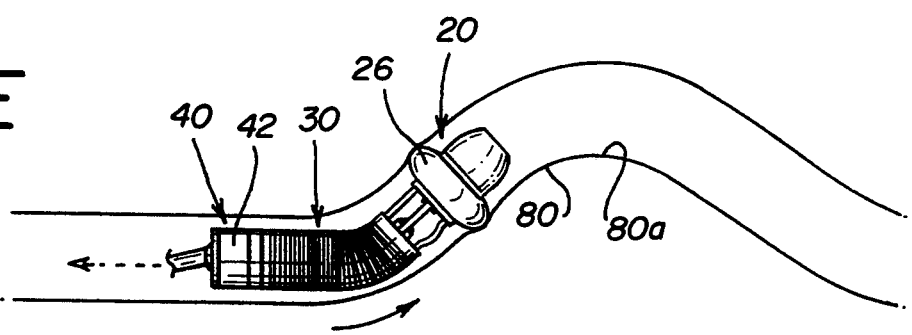

As shown in FIG. 6, the third solenoid valve 56c is first actuated to allow pressurized air to communicate with the recess 44f. As pressurized air enters the recess 44f, the third bladder 42 expands and engages with the intraluminal wall 80a of the body part 80, see FIG. 7B. The first valve 56a is then actuated to vent pressurized air in the first bladder 26 to atmosphere. At approximately the same time that the first bladder 26 is vented or soon thereafter, the second valve 56b is actuated to allow pressurized air to enter into the second bladder 32. This results in axial expansion of the second bladder 32 and, hence, axial movement of the distal section 20 from the proximal section 40, see FIG. 7C. Thereafter, the first valve 56a is actuated to allow pressurized air to communicate with the recess 28c, causing the first bladder 26 to expand and engage with the intraluminal wall 80a, see FIG. 7d. The second and third valves 56b and 56c are then actuated to vent the second and third bladders 32 and 42 to atmosphere, causing the proximal section 40 to move toward the distal section 20 under the influence of the spring 39. The actuation process is repeated by the controller 58 to effect continued migration of the distal, intermediate and proximal sections 20, 30 and 40 through the lumen of the tubular body part 80. To propel the distal, intermediate and proximal sections 20, 30 and 40 in the opposite direction, the process is reversed.

In accordance with a second embodiment of the present invention, the distal section 20 of the medical instrument 10 is provided with a second portion 110 comprising an anvil shroud 112, an axicon reflector 114, a window collar 116 and a focusing lens 117. The window collar 116 serves to house the focusing lens 117 and the distal end of a bundle of optical fibers 118 encased within a sheath 119, see FIGS. 8 and 9. The distal end 119a of the sheath is securely seated within an opening 116a in the proximal end 116b of the window collar 116. The diameter of the bundle of fibers 118 is approximately 1 millimeter.

A first portion of the optical fibers 118 comprises approximately 2–10 illumination fibers 118a. The illumination fibers 118a serve as flexible light guides. A second portion of the optical fibers 118 comprises approximately 10,000 separate imaging fibers 118b. The imaging fibers 118b act as a flexible image carrier. The illumination and imaging fibers 118a and 118b extend through the first, second and third members 28, 34 and 44. The proximal ends of the illumination fibers 118a are associated with an external light source (not shown). The proximal ends of the imaging fibers 118b are positioned adjacent to a focusing lens 119 which, in turn, is positioned adjacent to a charge coupled device (CCD) 134, see FIG. 9.

The axicon reflector 114 has a reflective outer surface 114b which acts to reflect light 130 from the illumination fibers 118a approximately 90° from the longitudinal axes of the fibers 118a onto a generally annular portion of the intraluminal wall 122 of the tubular body part 120, see also FIG. 10. The reflector 114 further serves to reflect an annular image 132 of the intraluminal wall 122 onto the imaging fibers 118b. The fibers 118b carry the image to the lens 119l which, in turn, focuses the image onto the CCD 134. The CCD 134 defines a plurality of pixels which sense the image light and generate voltage signals in response thereto. Those voltage signals are transmitted to a processing unit 136, which is used in conjunction with the CCD 134.

The annular image sensed by the CCD 134 appears confusing and distorted to an unskilled observer. To allow the annular image to be more easily interpreted, it is linearized by the processing unit 136. The linearization of the annular image is much the same as interpreting the image of a three dimensional sphere, such as a globe, as a two dimensional image on paper, such as a map. The image mapping that needs to be performed for linearization requires rolling the annular image along its outer circumference while stretching all of the off-equator points to map out a rectangular-shaped image. This can be performed simply by multiplying individual pixels by a vector multiplier comprising a distance and direction for each individual pixel of the image.

For the linearization operation, the processing unit 136 may utilize one of a number of commercially available software programs, such as Image Master, commercially available from Black Belt Systems, Inc., Glasgow, Mont., or Lightwave 3-D, commercially available from NewTek Incorporated, Topeka, Kans. These software programs are provided with algorithms in a menu driven or image manipulation format. Thus, an operator may accomplish image manipulation by hand with an input device such as a digitizing pen, mouse, joystick, or trackball.

While it would be possible for each image to be linearized manually by the current operator, it is more expedient and currently preferred for a calibrating linearization operation to be performed for an instrument to thereby develop a series of vector multipliers. After the vector multipliers are developed for a given instrument, they can then be used to linearize images thereafter unless the optical characteristics of the instrument are changed.

For a standard video image of 640 by 480 pixels the resulting matrix is approximately 300,000 multiplication operations for linearization of an image. While a large number of operations are involved, at processing rates of 20–60 megahertz, the linearization operation does not represent any time delays for a dedicated image processing unit.

It is also contemplated by the present invention that a linearization algorithm in a numeric format may also be used. The numeric format depends upon predefined equations for characterizing the optical characteristics of an instrument and, as a consequence, requires more precise production of the optical system and with the current state of technology, may not be practical. In any event, the processing unit 136 thus generates a linearized video signal which is passed to a monitor 138 for viewing by the current user.

The monitor 138 displays a picture of the annular portion of the intraluminal wall 122 sensed by the CCD 134 which is modified as described to facilitate interpretation of the image by an operator. Thus, a physician, by viewing the monitor 138, can make a 360° visual inspection of an annular portion of the intraluminal wall 122 of the body part 120. This is particularly advantageous, when, for example, first and second sections 120a and 120b of the tubular body part 120 have been joined together by a plurality of staples 140, see FIG. 9. The staples 140 are applied by a known anastomotic stapler. Use of the axicon reflector 114 after stapling permits the surgeon to inspect the annular line of staples 140 and adjacent tissue to ensure that a proper anastomosis has been formed.

Figure 11:
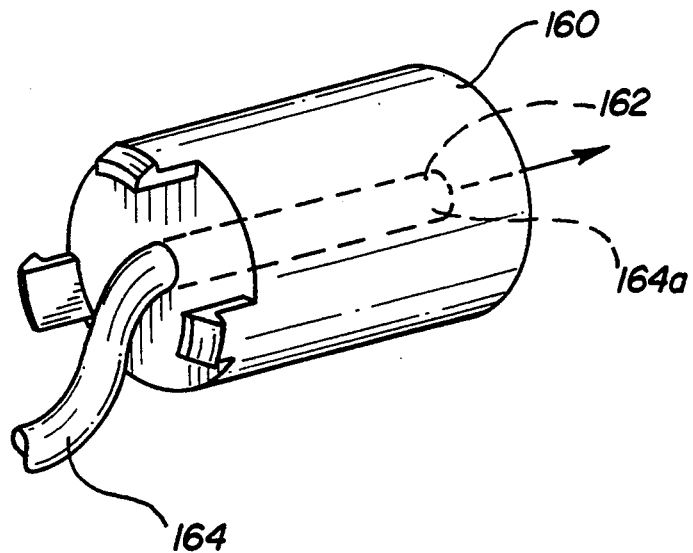
FIG. 11 is a perspective view of a second portion of the distal section of a medical instrument constructed in accordance with a third embodiment of the present invention.

In accordance with a third embodiment of the present invention, the distal section 20 is provided with a second portion 160 having an internal bore 162 for receiving the distal end 164a of a delivery conduit 164, see FIG. 11. The proximal end (not shown) of the conduit 164 is associated with an external supply source. The supply source may comprise a pneumatic supply source for injecting air through the conduit 164 into the lumen of a tubular body part for expanding the intraluminal wall of the tubular body part. Water, medication or a radiopaque agent can also be injected via an appropriate supply source through the conduit 162 for delivery to a desired portion of the tubular body part. It is also contemplated that a vacuum means (not shown) may be used in conjunction with the conduit 162 for removing fluid, tissue and the like from within a tubular body part.

Figure 12:
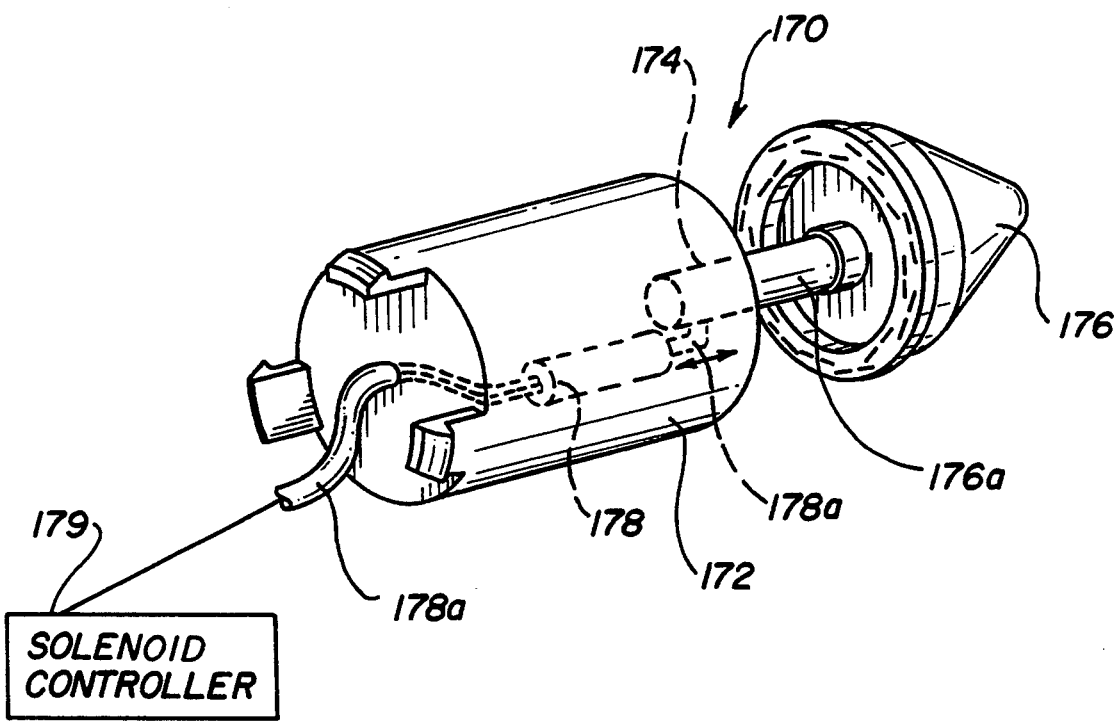
FIG. 12 is a perspective view of a second portion of the distal section of a medical instrument constructed in accordance with a fourth embodiment of the present invention.

In accordance with a fourth embodiment of the present invention, the distal section 20 of the medical instrument 10 is provided with a second portion 170 comprising a housing member 172 which may be formed from the same material from which the first member 28 is formed, see FIG. 12. The housing member 172 is snap-fitted onto the first member 28. The housing member 172 includes an internal bore 174 for receiving the shaft 176a of an anvil 176 which, for example, may comprise the anvil of an anastomotic stapler (the remaining section of the stapler is not shown). Fixedly mounted within the housing 172 is a solenoid 178 having a reciprocating plunger 178a. The plunger 178a, when in its extended position, frictionally engages with the shaft 176a to retain the shaft 176a in the bore 174. A solenoid controller 179 is connected to the solenoid 178 via conductors 178a and serves to actuate the solenoid 178 to effect reciprocating movement of the plunger 178a. The solenoid controller 179 may comprise a switch, a joystick or other like control mechanism. It will be apparent to those skilled in the art that the second portion 170 may be modified so that it can releasably retain other tools (not shown) and deliver same into the lumen of a tubular body part via the medical instrument of the present invention.

It is further contemplated by the present invention that the distal section 20 of the instrument 10 may be provided with a second portion having end effectors such as graspers, dissectors, scissors or other basic surgical instruments.

Figure 13:
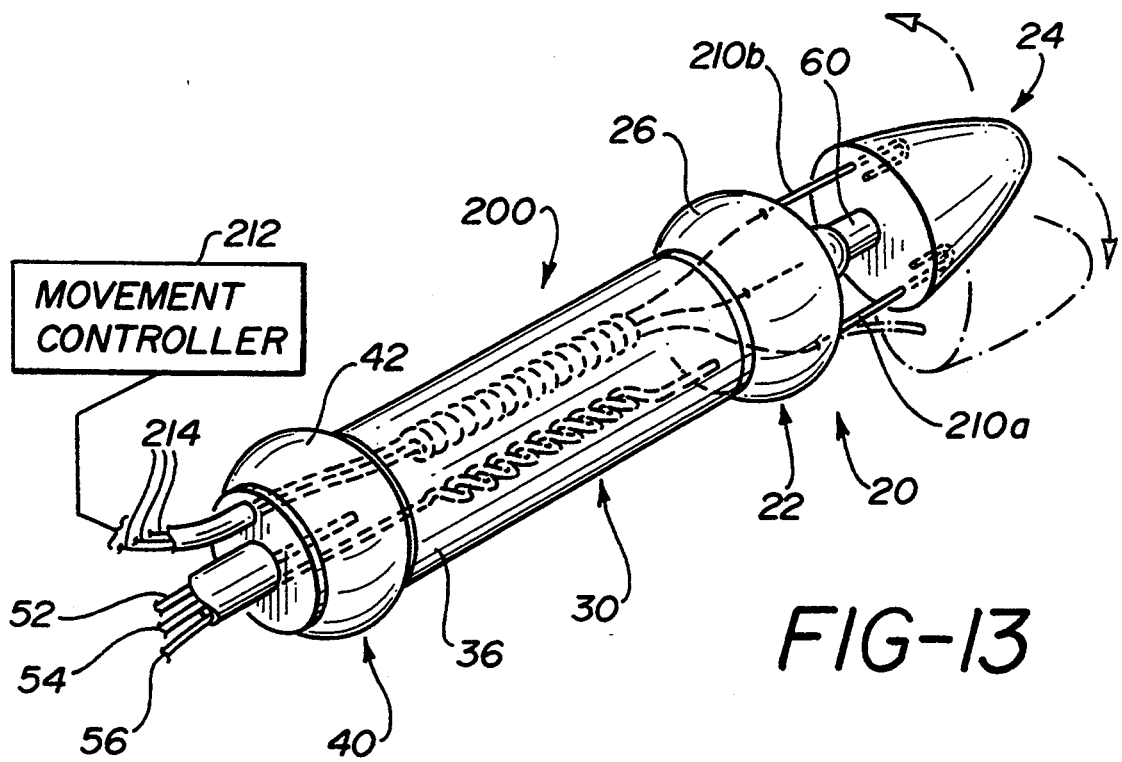
FIG. 13 is a perspective view of distal, intermediate and proximal sections of a medical instrument constructed in accordance with a fifth embodiment of the present invention; and, FIG. 14 is a perspective view of the distal section and a portion of the intermediate section of the medical instrument illustrated in FIG. 13 with different angular positions of the second portion of the distal section shown in phantom.
Figure 14:
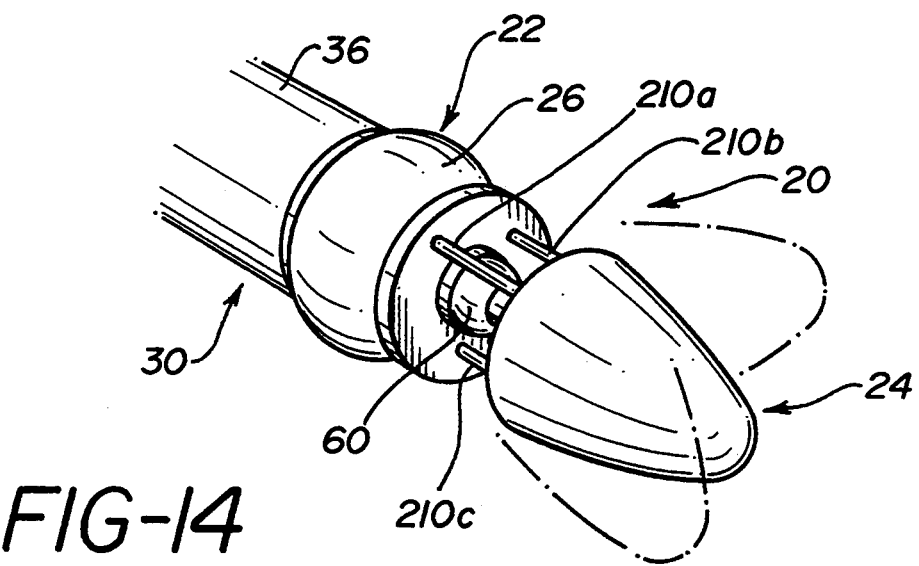

The medical instrument 200, formed in accordance with a further embodiment of the present invention, is shown in FIGS. 13 and 14, where like elements are referenced by like numerals. In this embodiment, the ball and socket coupler 60 is interposed between the first and second portions 22 and 24 of the distal section 20. Thus, the first and second members 28 and 34 (not shown in FIGS. 13 and 14) are either formed as a single unit or secured to one another by conventional attachment means, such as adhesive. The second portion 24 is only schematically illustrated, but may comprise any one of the second portions discussed above.

Further coupled between the first and second portions 22 and 24 are three shape-memory-alloy wires 210a–210c, nitinol wires in the illustrated embodiment. A movement controller 212 is connected to the wires 210a–210c via conductors 214 and serves to pass current through one or more of the wires 210a–210c to effect angular movement of the second portion 24 about the coupler 60. The movement controller 212 may comprise three switches, a joystick or other like control mechanism.

As current passes through one of the wires 210a–210c, the wire changes its length, i.e., it lengthens. Thus, a physician, via the controller 212, can control which of the three wires 210–210c receives current and thereby effect angular movement of the second portion 24 about the coupler 60 as the second portion 24 encounters bends and turns during its movement through the length of a tubular body part.

Having described the invention in detail and by reference to preferred embodiments thereof, it will be apparent that modifications and variations are possible without departing from the scope of the invention defined in the appended claims. For example, it is contemplated by the present invention that separate vacuum means (not shown) may be used in place of the first and third bladders 26 and 42 for engaging with the intraluminal wall of the tubular body part. It is further contemplated that the instrument of the present invention may be used in non-medical applications where it would be desirable to perform operations similar to the ones noted above within a tubular part such as a pipe, conduit, etc.

What is claimed is:

1. An elongated medical instrument defining a longitudinal axis along its length adapted for migration through a lumen of a tubular body part having an intraluminal wall comprising:
   a distal section including distal means for engaging and disengaging the intraluminal wall of the tubular body part;
   a proximal section including proximal means for engaging and disengaging the intraluminal wall of the tubular body part;
   an intermediate section connected to said proximal section and including intermediate means for expanding and contracting along said longitudinal axis of the instrument to effect movement of at least one of said distal and proximal sections;
   means interposed between said distal and intermediate sections for movably coupling said distal section to said intermediate section; drive means coupled between said distal and intermediate sections for effecting movement of said distal section about said coupling means; and
   means for selectively engaging and disengaging said distal and proximal means with the intraluminal wall and expanding and contracting said intermediate means to effect migration of said distal, intermediate and proximal sections through the lumen.

2. An elongated medical instrument as set forth in claim 1, wherein said distal section includes a medical device.

3. An elongated medical instrument as set forth in claim 2, wherein the medical device comprises means for delivering fluid into the lumen of said tubular body part.

4. An elongated medical instrument as set forth in claim 3, wherein the fluid comprises air for inflating said tubular body part.

5. An elongated medical instrument as set forth in claim 2, wherein said medical device comprises means for delivering therapy to a portion of the tubular body part.

6. An elongated medical instrument as set forth in claim 2, wherein said medical device comprises means for delivering a radiopaque agent to a portion of the tubular body part.

7. An elongated medical instrument as set forth in claim 2, wherein said medical device comprises imaging means for viewing the tubular body part for inspection thereof.

8. An elongated medical instrument as set forth in claim 2, wherein said medical device comprises optical means for permitting annular imaging of the intraluminal wall of the tubular body part for inspection thereof.

9. An elongated medical instrument as set forth in claim 1, wherein said drive means comprises one or more solenoids.

10. An elongated medical instrument as set forth in claim 1, wherein said drive means comprises one or more shape-memory-alloy wires.

11. An elongated medical instrument as set forth in claim 10, wherein said one or more shape-memory-alloy wires comprise one or more nitinol wires.

12. An elongated instrument as set forth in claim 1, wherein
   said distal means comprises a distal bladder adapted to be radially expanded and contracted;
   said proximal means comprises a proximal bladder adapted to be radially expanded and contracted; and
   said intermediate means comprises an intermediate bladder adapted to be axially expanded and contracted and means for biasing said distal and proximal sections toward one another.

13. An elongated medical instrument defining a longitudinal axis along its length adapted for migration through a lumen of a tubular body part having an intraluminal wall comprising:
   a distal section including a first portion having distal means for engaging and disengaging the intraluminal wall of the tubular body part and a second portion located distally of said first portion;
   a proximal section including proximal means for engaging and disengaging the intraluminal wall of the tubular body part;
   an intermediate section connected to said distal and proximal sections including intermediate means for axially expanding and contracting along said longitudinal axis of the instrument to effect movement of at least one of said distal and proximal sections;
   drive means connected to said distal section and located between said distal and intermediate sections for causing said distal section to move with respect to said longitudinal axis of the instrument; and
   means for selectively engaging and disengaging said distal and proximal means with the intraluminal wall and expanding and contracting said intermediate means to effect migration of said distal, proximal and intermediate sections through the lumen.

14. An elongated medical instrument as set forth in claim 13, wherein said distal means includes a medical device.

15. An elongated medical instrument as set forth in claim 14, wherein said medical device comprises means for delivering fluid into the lumen of the tubular body part.

16. An elongated medical instrument as set forth in claim 14, wherein said medical device comprises means for delivering medication to a portion of the tubular body part.

17. An elongated medical instrument as set forth in claim 14, wherein said medical device comprises means for viewing the tubular body part for inspection thereof.

18. An elongated medical instrument as set forth in claim 14, wherein said medical device comprises optical means for permitting annular imaging of the intraluminal wall of the tubular body part for inspection thereof.

19. An elongated medical instrument as set forth in claim 13, wherein said drive means comprises one or more solenoids.

20. An elongated medical instrument as set forth in claim 13, wherein said drive means comprises one or more shape-memory-alloy wires.

21. An elongated medical instrument as set forth in claim 20, wherein said one or more shape-memory-alloy wires comprise one or more nitinol wires.

22. An elongated medical instrument as set forth in claim 13, wherein said distal means comprises a distal bladder adapted to be radially expanded and contracted;

said proximal means comprises a proximal bladder adapted to be radially expanded and contracted; and said intermediate means comprises an intermediate bladder adapted to be axially expanded and contracted and means for biasing said distal and proximal sections toward one another.

23. An elongated instrument defining a longitudinal axis along its length adapted for migration through a tubular part having an inner wall comprising:

a distal section including a first portion having distal means for engaging and disengaging the inner wall of the tubular part and a second portion located distally of said first portion;

a proximal section including proximal means for engaging and disengaging the inner wall of the tubular part;

an intermediate section connected to said distal and proximal sections including intermediate means for axially expanding and contracting along said longitudinal axis of the instrument to effect movement of at least one of said distal and proximal sections;

drive means located between said distal and intermediate sections for causing said distal section to move with respect to said longitudinal axis of the instrument; and means for selectively engaging and disengaging said distal and proximal means with said inner wall and expanding and contracting said intermediate means to effect migration of said distal, proximal and intermediate sections through the tubular part.

* * * * *